United States Patent [19]

Becker et al.

[11] 4,429,040
[45] Jan. 31, 1984

[54] METHOD AND REAGENT FOR THE DETECTION OF FIBRIN MONOMER

[75] Inventors: Udo Becker, Munich; Peter Roeschlau, Seeshaupt, both of Fed. Rep. of Germany

[73] Assignee: Boehringer Mannheim GmbH, Mannheim-Waldhof, Fed. Rep. of Germany

[21] Appl. No.: 256,212

[22] Filed: Apr. 21, 1981

[30]     Foreign Application Priority Data

May 8, 1980 [DE]  Fed. Rep. of Germany ....... 3017707

[51] Int. Cl.³ .................... G01N 33/54; C12Q 1/56
[52] U.S. Cl. .................................. 435/7; 435/13
[58] Field of Search .............. 435/4, 7, 13, 23, 24, 435/180, 181, 810; 23/230 B; 424/1, 12; 436/533

[56]          References Cited
U.S. PATENT DOCUMENTS

| | | | |
|---|---|---|---|
| 3,088,875 | 5/1963 | Fisk | 435/7 |
| 4,090,846 | 5/1978 | Buck | 23/230 B |
| 4,181,636 | 1/1980 | Fischer | 435/7 |
| 4,208,185 | 6/1980 | Sawai et al. | 435/7 |

OTHER PUBLICATIONS

Wilner et al., J. Lab. Clin. Med., vol. 97, No. 3, pp. 403-411 (Mar. 1981).
Nihei et al., "Fibrin Degradation Product (FDP) Determination in Urine by FDP Latex Test-U", Chem. Abstracts, vol. 93, No. 3, p. 337, (1980), abst. No. 22064w.
Someraro, "Fibrinogen, Fibrinopeptide A and Fibrin Monomers," Acta Clinica Belgica, vol. 32, No. 6 (1977) pp. 380-385.
Nihei et al., "Fibrin Degradation Product (FDP)"Determination in Urine" by FDP Latex Test-U, Shindan to Chiryo, vol. 68, No. 3 (1980), pp. 558-560.

Primary Examiner—Thomas G. Wiseman
Assistant Examiner—Frederick W. Pepper
Attorney, Agent, or Firm—Felfe & Lynch

[57]           ABSTRACT

The present invention provides a process for the detection or determination of fibrin monomer in biological fluids, wherein the sample fluid is incubated with hydrophobic latex and the agglutination determined.

The present invention also provides a reagent for the detection or determination of fibrin or fibrin monomer in biological fluids, wherein it contains hydrophobic latex.

8 Claims, No Drawings

METHOD AND REAGENT FOR THE DETECTION OF FIBRIN MONOMER

This invention relates to a method and a reagent for the detection and determination of fibrin monomer (FS) in blood plasma and other biological fluids.

The early recognition of a tendency to thrombosis is of great diagnostic importance. For this purpose, latently proceeding coagulation processes, which have still not led to an externally visible clinical picture, must be recognized. Hitherto, no sensitive or clinically practicable methods were available for detecting activation products of the coagulation system in a simple manner. One of the direct indicators for the course of coagulation processes is FS which results from the action of thrombin on fibrinogen. Small amounts of FS are stabilized by fibrinogen present in excess in the blood and are kept in solution, without a deposition occurring in the blood vessel system. Therefore, it is the object of a diagnostic process to detect and determine small amounts of this FS, circulating in soluble form, in the presence of an excess of fibrinogen. Since FS cannot be distinguished from fibrinogen either by the molecular weight or by the antigen structure, the usual biochemical detection processes cannot be used. The following methods are already known for the detection of FS:

1. Precipitation processes which utilize the greater tendency of the FS to precipitate in comparison to fibrinogen, for example, the ethanol test of Breen and Tullis (see Annals of Internal Medicine, 69, 1197–1206/1968) or the protamine sulphate test of Niewiarowski and Gurewich (see J. Lab. Clin. Med., 77, 665–676/1971). For a better recognition of the flocculating out fibrin filaments, colloidal colored particles are added, for example soot particles (see Federal Republic of German Patent Specification No. 25 28 381). Besides the danger of non-specific precipitation, these methods have the disadvantage of being insensitive and of only giving qualitative indications.

2. Gel exclusion chromatography (see Fletcher and Alkjaersig in Recent Advances in Thrombosis, ed. L. Poller, London 1973, pub. Livingstone-Churchill) and affinity chromatography with fibrin agarose (see Heene and Matthias, Thromb. Research, 2, 137–154/1973). These methods are based on the ability of FS to form high molecular weight complexes with fibrinogen or on the self-association of FS. They are not to be regarded as being routine clinical methods because they are not practical and are also not sufficiently sensitive.

3. A process is also known which depends upon the self-association of FS (see Largo, Heller and Straub in Blood, 47 (6), (June 1976)) in which erythrocytes laden with FS are first produced which then agglutinate in the presence of the dissolved FS in a sample to be investigated. This process has also not established itself as a clinical test, especially because of its insufficient sensitivity.

4. Incorporation of $^{14}C$ glycine esters (see Kisker and Rush, J. Clin. Invest., 50, 2235/1971). Radioactively-marked $^{14}C$ glycine esters can be specifically incorporated into FS with the help of Factor XIII. The process is sensitive but not very practical and requires the usual laborious measures and expensive apparatus required when dealing with radioactivity.

It is an object of the present invention to overcome the disadvantages of the known processes and to provide a process of the above-mentioned kind which can be carried out simply and quickly, which does not require any expensive devices and can be used not only for qualitative and semi-quantitative determinations but also for quantitative determinations.

Surprisingly, we have now found that fibrin monomer (FS), in contradistinction to fibrinogen and other plasma proteins, displays a high affinity towards hydrophobic latex particles.

Thus, according to the present invention, there is provided a process for the detection or determination of fibrin monomer in biological fluids, wherein the sample fluid is incubated with latex and the agglutination determined.

According to the present invention latices are preferably used, the particles or droplets of which have an average diameter of 0.05 to $1.5\mu$ and especially preferably of 0.5 to $1.2\mu$ in the case of measurement in an aggregation measurement device and of 0.07 to $0.1\mu$ in the case of measurement in a photometer. However, latices or droplets can also be used with a diameter lying outside of these ranges. Thus, useful results have also been obtained with latex particles of $0.03\mu$ and of $10\mu$ diameter. Within the scope of the present invention, by a latex there is to be understood an emulsion or other dispersion of natural or synthetic rubber particles, especially the polymer and co-polymer particles dispsersed in water, for example of styrene or styrene and butadiene. It is important for the present invention that the particles or droplets have a hydrophobic surface.

The incubation of the sample fluid with the latex is preferably carried out at an elevated temperature, a temperature of from 30° to 40° C. being preferred, since the reaction then takes place the most quickly. However, lower temperatures can also be used but with correspondingly longer periods of incubation or possibly also somewhat higher temperatures. The pre-incubation time at a temperature of 37° C. is preferably 5 to 15 minutes. When going below this range, the reproducibility becomes questionable and exceeding it does not provide any advantages.

The reaction is preferably carried out in a buffered solution, pH values of from 7.0 to 9.0 having proved to be especially suitable. pH values of from 7.7 to 8.7 are preferred. For the adjustment of the desired pH range, use can be made of any desired buffer substances which are effective in the mentioned range, a glycine/sodium chloride buffer being preferred. The buffer concentration is preferably from 0.05 to 0.5 M.

The qualitative carrying out of the process according to the present invention is preferably performed in such a manner that the sample to be investigated, for example plasma, is incubated with an appropriate aqueous suspension of latex particles, the above-mentioned temperature and time range preferably being used.

The reaction mixture is subsequently carefully shaken or is dropped on to a test plate, which can be divided up into individual fields and which can be transparent or also, for better observation, can have a dark base, the test base plate being moved rotationally. When FS is present in the fluid being investigated, agglomeration of the particles results, which can be seen macroscopically. For making the reaction better visible, the particle suspension can also be centrifuged, the agglutinated particles then sedimenting more quickly and easily than the non-agglutinated ones. The reaction can also be advantageously carried out in micro-titration plates which, for acceleration of the reading, can be additionally centrifuged.

For the semi-quantitative carrying out of the process, serial dilutions are prepared and these are compared with a sample which contains a known amount of FS. The highest dilution step which still results in a visible agglutination is hereby preferably multiplied with the limit of detection of the reaction. This limit of detection can be determined by the use of a standard with a known FS content in the same manner by diluting out. The process can be carried out quantitatively by using an aggregation measurement device or a photometer.

By fibrin, which can be determined by the process according to the present invention, there is to be understood that so-called soluble fibrin, i.e. an intermediate form of fibrin in the case of which the fibrin monomer in the actual sense has already come together to form fibrils but on the surface either still carries true fibrin monomer or, in any case, behaves like fibrin monomer. This soluble fibrin also leads to the same agglutination and is, therefore, also determined by the test process.

The present invention also provides a reagent for the detection or determination of fibrin monomer in biological fluids, which reagent contains hydrophobic latex particles.

The latex preferably has a particle content of from 0.1 to 10% and more preferably of from 0.5 to 5%. The latex and sample solution can be mixed in a volume ratio of from about 1:10 to 10:1. If a 1% suspension is used, then the mixing ratio is preferably from 2:1 to 1:2.

The present invention is also useful for the indirect determination of fibrinogen. In this case, all the fibrinogen of the sample is first converted in known manner into fibrin monomer, the conversion being carried out with an appropriate enzyme, for example, thrombin or snake venom, for example batroxobin. If, in a parallel sample, the content of fibrin monomer is ascertained, then, from the difference between the determined FS content in the comparison sample and that of the sample treated with the enzyme, there is given the fibrinogen content. In the case of this embodiment of the present invention, the conversion of the fibrinogen into fibrin monomer is preferably carried out in the presence of the latex particles.

The following Examples are given for the purpose of illustrating the present invention:

EXAMPLE 1

A. Blood is taken from a healthy subject, with the addition of 1 mg./ml. EDTA and 0.1 mg./ml. aprotonin and centrifuged for 10 minutes at 2000 g. 1 ml. of the supernatant of blood plasma is adjusted to 37° C. and mixed with 0.05 U of thrombin (Topostasin, Roche). 0.2 ml. Aliquots are removed at definite times and pipetted into prepared tubelets which contain 5 U heparin (Liquemin, Roche) and 0.2 U hirudin (Sigma) (stopwatch reaction). As time points for taking the aliquots, there are chosen: immediately after the addition of the thrombin, 30 seconds, 1 minute, 2 minutes and 5 minutes. Samples containing different amounts of FS are thus obtained which are kept at ambient temperature for the further investigations.

B. Dilutions of the samples are prepared in a glycine-sodium chloride buffer which contains 0.25 mole glycine and 0.9% sodium chloride and which has been adjusted with 1 N aqueous sodium hydroxide solution to a pH value of 8.2. A polystyrene latex (Serva, Heidelberg) in the form of a 10% suspension with an average particle diameter of 0.8μ is diluted 1:10 with the same buffer. 0.05 ml. amounts of the latex and 0.05 ml. amounts of plasma sample pre-diluted in an appropriate manner are mixed and incubated for 10 minutes at 37° C. The contents of the tubelet are applied to individual fields, separated from one another, of a dark lacquered synthetic resin plate and the plate is rotated carefully for 2 minutes and subsequently the agglomeration of the latex particles is recorded. It is found that with increasing period of time of the action of the thrombin on the plasma, the intensity of the agglomeration increases. By the use of increasing dilutions, that dilution can be given for each sample at which a distinct agglutination still just takes place. The results obtained are given in the following Table 1:

TABLE 1

| period of treatment with thrombin (min.) | sample | titer |
| --- | --- | --- |
| 0 | plasma | 1:16 |
| 0.5 | plasma | 1:64 |
| 1 | plasma | 1:1600 |
| 2 | plasma | 1:6400 |
| 5 | plasma | 1:25600 |
| 0 | buffer | negative |
| 0 | undiluted serum | negative |

A blank carried out with buffer or serum did not give any agglutination at all.

EXAMPLE 2

The FS-containing samples prepared according to Example 1 are diluted with glycine-sodium chloride-containing buffer to which 1% bovine serum albumin had additionally been added. The results obtained are given in the following Table 2:

TABLE 2

| period of treatment with thrombin (min.) | sample | titer |
| --- | --- | --- |
| 0 | plasma | 1:8 |
| 0.5 | plasma | 1:32 |
| 1 | plasma | 1:128 |
| 2 | plasma | 1:256 |
| 5 | plasma | 1:512 |
| 0 | buffer | negative |
| 0 | serum | negative |

EXAMPLE 3

A solution of FS in 3 mole urea solution, 50 mMole tris, 5 mMole EDTA and 0.01% aprotonin (pH 7.4) was prepared according to the procedure of Mahn et al. (see Thromb. Res., 14, 651–663/1979) and the content of FS determined, after dilution with 0.1 N aqueous sodium hydroxide solution, by means of the optical density at 280 nm. Plasma obtained according to Example 1 is diluted 1:8 with glycine/sodium chloride (pH 8.2). By the addition of increasing amounts of urea-containing FS solution, samples with a definite content of FS are prepared, namely, 0, 5, 10 and 50 μg./ml., volume compensation taking place by means of FS-free urea solution. The samples are incubated, analogously to Example 2, with the latex suspension and the last dilution stage which still results in an agglutination reaction is ascertained. The results from two independent determinations are summarized in the following Table 3:

TABLE 3

| FS concentration μg./ml. | titer | limit of detection μg./ml. |
|---|---|---|
| 5 | 1:4 | 1.3 |
| 10 | 1:10 | 1.0 |
| 50 | 1:40 | 1.3 |

From the individual limiting dilutions which just lead to a positive agglutination, there can be calculated the limit of detection for FS by multiplication of the particular FS concentration with the dilution. On average, a limit of detection of about 1.2 μg./ml. is obtained.

Example 4

A fibrinogen solution with a content of 500 mg./dl. and a human citrated plasma with a fibrinogen content of 180 mg./dl. is diluted 1:100 with a glycine-sodium chloride buffer (pH 8.2) which contains 1% bovine serum albumin. Starting therefrom, further serial dilutions of 1:2, 1:4 and so forth are prepared in the same buffer and 0.1 ml. thereof pipetted into tubelets. To each of these tubelets are successively added 0.1 ml. of a solution of batroxobin (Reptilase reagent, Boehringer Mannheim GmbH) diluted 1:10 with a 0.9% aqueous solution of sodium chloride and 0.1 ml. of a latex prepared according to Example 1 and the tubelets are then incubated for 10 minutes at 37° C. The agglutination titer is subsequently determined by dropping on to a test plate. For the fibrinogen solution there is found 1:16 and for the plasma 1:8, which, having regard to the pre-dilution of 1:100, corresponds to a dilution of 1:1600 and 1:1800, respectively. From this there is calculated a detection limit for fibrinogen of about 2.7 μg./ml.

EXAMPLE 5

Dilutions of a plasma in bovine serum albumin-containing glycine-sodium chloride buffer, prepared according to Example 1 and treated with thrombin for 5 minutes, are incubated at 37° C. with the latex suspension for various periods of time and the agglutination titer then determined. However, it is found that the sensitivity no longer increases after a period of incubation of 10 minutes.

EXAMPLE 6

As FS solution in 3 M urea solution is prepared according to Example 3. A fibrinogen solution in glycine/sodium chloride buffer (pH 8.2), with a fibrinogen content of 2 mg./ml., is divided up into 5×1 ml., brought to 37° C. and the aliquots mixed with increasing amounts of the FS solution so that contents of 10, 20, 30, 40 and 50 μg./ml. result.

A commercially available aggregometer (Braun/Melsungen) with a recorder, such as is conventionally used for the measurement of thrombocyte aggregations, is subsequently provided with an adjustable stirrer device.

The following run is carried out: filter 546 nm., 37° C., stirring speed 500 r.p.m. 1 ml. Glycine-sodium chloride buffer is prepared and the temperature adjusted to 37° C. 0.1 ml. of a 1% latex suspension in glycine/sodium chloride buffer is added thereto and the extinction of 1.9 adjusted on a photometer. 50 μl. amounts of the above-described fibrinogen solutions are added thereto. The agglutination of the latex particles leads to a clarification in the solution, which is recorded by the recorder. The experiment is successively carried out with all FS concentrations and subsequently with the fibrinogen solution without the addition of FS and a buffer blank value. It is found that the fibrinogen solution used already has a certain FS content since, even without the addition of FS, a clearing up of the turbidity is ascertained. The maximum decreases of extinction of the aggregometer are plotted against the FS concentration, a linear relationship being obtained, from which the reaction sensitivity is to be read off as the slope. There is found 14 mE/μg. FS. Furthermore, this slope can be used for the determination of the FS already present in the fibrinogen solution used. There are found 51 μg./ml., 2.6% of the fibrinogen content.

EXAMPLE 7

In a commercially available photometer, provided with an automatic cuvette changing device for 6 cuvettes and a recorder, there is carried out the following run: filter 405 nm., 37° C., 1 cm. semimicrocuvettes.

Into each of the 6 cuvettes, there is placed 1 ml. of glycine-sodium chloride-serum albumin buffer (pH 8.2) and the temperature equilibrated to 37° C. Into each of the cuvettes 1 to 6 are placed 100 μl of the thrombin-treated plasma samples prepared according to Example 1 and mixed. To each batch there is then added 0.1 ml. of a latex suspension (Serva, average particle diameter 0.085μ), pre-diluted to 0.5%, in glycine-sodium chloride buffer (pH 8.2), mixed and the cuvette changer and the recorder started simultaneously. The batches show a linear increase of extinction, depending upon the period of treatment with thrombin, which is given numerically in the following Table 4:

| period of treatment with thrombin (sec.) | increase of extinction (ΔE/min.) |
|---|---|
| 0 | 0 |
| 30 | 0.011 |
| 60 | 0.049 |
| 90 | 0.090 |
| 180 | 0.130 |
| 300 | 0.144 |

It will be understood that the specification and examples are illustrated but not limitative of the present invention and that other embodiments within the spirit and scope of the invention will suggest themselves to those skilled in the art.

What is claimed is:

1. Method for the determination of fibrin monomer in a biological fluid sample comprising incubating said fluid sample with a reagent consisting essentially of hydrophobic latex under conditions suitable for agglutination, and determining the resulting agglutination as a measure of fibrin monomer content in the sample.

2. Method as claimed in claim 1, wherein said hydrophobic latex has an average particle diameter of from 0.05 to 1.5μ.

3. Method as claimed in claim 1, wherein the incubation is carried out at a temperature of from 30° to 40° C. for 5 to 15 minutes.

4. Method as claimed in claim 1, wherein the incubation is carried out in a buffered solution at a pH of from 7.0 to 9.0.

5. Method as claimed in claim 1, wherein, the sample, after incubation with the latex, is applied to a dark-colored test plate and the agglutination ascertained, to result in a qualitative determination.

6. Method as claimed in claim 1, wherein serial dilutions of the sample fluid are prepared and compared with a standard with a known content of FS, to result in a quantitative determination.

7. Method as claimed in claim 1, wherein the change of turbidity brought about by the agglutination is measured optically, to result in a quantitative determination.

8. Method as claimed in claim 1, wherein, the fibrinogen present in the sample fluid is first converted into FS with the use of thrombin or of a snake venom enzyme.

* * * * *